(12) United States Patent
Nuwayser

(10) Patent No.: US 7,157,102 B1
(45) Date of Patent: Jan. 2, 2007

(54) MULTI-LAYERED MICROCAPSULES AND METHOD OF PREPARING SAME

(75) Inventor: Elie S. Nuwayser, Woburn, MA (US)

(73) Assignee: Biotek, Inc., Woburn, MA (US)

( * ) Notice: Subject to any disclaimer, the term of this patent is extended or adjusted under 35 U.S.C. 154(b) by 170 days.

(21) Appl. No.: 10/161,130

(22) Filed: May 31, 2002

(51) Int. Cl.
*A61K 9/16* (2006.01)
*A61K 9/14* (2006.01)

(52) U.S. Cl. ............... 424/490; 424/489; 424/497; 424/452; 424/463

(58) Field of Classification Search ........... 424/451, 424/452, 455, 463, 458
See application file for complete search history.

(56) References Cited

U.S. PATENT DOCUMENTS

| | | | |
|---|---|---|---|
| 3,523,906 A | 8/1970 | Hova et al. ............ 252/316 |
| 3,691,090 A | 9/1972 | Kitajima et al. ........ 252/316 |
| 3,737,337 A | 6/1973 | Wuppertal-Elberfeld et al. .... 117/100 |
| 3,891,570 A | 6/1975 | Fukushima et al. ...... 252/316 |
| 3,960,757 A | 6/1976 | Morishita et al. ....... 252/316 |
| 4,384,975 A * | 5/1983 | Fong .................. 427/213.36 |
| 4,389,330 A * | 6/1983 | Tice et al. ............ 427/213.36 |
| 4,499,096 A | 2/1985 | Lotsof ................. 514/214 |
| 4,530,840 A | 7/1985 | Tice et al. ............ 514/179 |
| 4,542,025 A | 9/1985 | Tice et al. ............ 424/78 |
| 4,568,559 A | 2/1986 | Nuwayser et al. ....... 427/3 |
| 4,582,835 A | 4/1986 | Lewis et al. ........... 514/282 |
| 4,588,580 A | 5/1986 | Gale et al. ............ 424/21 |
| 4,623,588 A | 11/1986 | Nuwayser et al. ...... 428/402.24 |
| 4,675,189 A | 6/1987 | Kent et al. ............ 424/490 |
| 4,861,627 A * | 8/1989 | Mathiowitz et al. .... 427/213.31 |
| 4,895,848 A | 1/1990 | Traber et al. .......... 514/255 |
| 4,897,268 A | 1/1990 | Tice et al. ............ 424/422 |
| 4,919,916 A | 4/1990 | Golwyn ................ 424/10 |
| 4,931,277 A | 6/1990 | Fontaine et al. ........ 424/195.1 |
| 4,935,428 A | 6/1990 | Lewis .................. 514/282 |
| 4,935,429 A | 6/1990 | Dackis et al. .......... 514/288 |
| 4,942,182 A | 7/1990 | Weiss et al. ........... 514/812 |
| 5,075,341 A | 12/1991 | Mendelson et al. ..... 514/282 |
| 5,100,669 A * | 3/1992 | Hyon et al. ........... 424/426 |
| 5,100,916 A | 3/1992 | Johansson et al. ...... 514/478 |
| 5,124,340 A | 6/1992 | Jaffe et al. ........... 514/356 |
| 5,140,032 A | 8/1992 | Radecki ............... 514/221 |
| 5,149,538 A | 9/1992 | Granger et al. ........ 424/449 |
| 5,223,497 A | 6/1993 | Gawin et al. .......... 514/225.2 |
| 5,240,711 A | 8/1993 | Hille et al. ........... 424/448 |
| 5,256,669 A | 10/1993 | Askanazi et al. ....... 514/282 |
| 5,272,149 A | 12/1993 | Stalling .............. 514/255 |
| 5,298,622 A | 3/1994 | Portoghese et al. ..... 546/15 |
| 5,407,609 A | 4/1995 | Tice et al. ........... 264/46 |
| 5,474,786 A * | 12/1995 | Kotwal et al. ......... 424/472 |

(Continued)

OTHER PUBLICATIONS

Amory et al., "Testosterone Release from a Subcutaneous, Biodegradable Microcapsule Formulation (Viatrel) in Hypogonadal Men," *J. Andrology*, 23(1):84-91 (2002).

(Continued)

*Primary Examiner*—Lakshmi Channavajjala
(74) *Attorney, Agent, or Firm*—Banner & Witcoff, Ltd.

(57) ABSTRACT

A multi-layered microcapsule containing one or more active ingredients and process for preparing the same is disclosed. The multi-layered microcapsule comprises an inner solid microparticle core, typically composed of a biodegradable polymer, and having one or more alternating layers of polymer, active ingredient or polymer/active ingredient mixtures to produce a multi-layered microcapsule wherein the polymer or active ingredient in each layer may be the same or different or have the same or different concentration of the polymer or active ingredient in other layers.

32 Claims, 9 Drawing Sheets

U.S. PATENT DOCUMENTS

| | | | |
|---|---|---|---|
| 5,648,097 A | | 7/1997 | Nuwayser .................... 424/489 |
| 6,123,965 A | * | 9/2000 | Jacob et al. ................. 424/489 |
| 6,306,425 B1 | | 10/2001 | Tice et al. .................. 424/426 |

OTHER PUBLICATIONS

Comer et al., "Depot naltrexone: long-lasting antagonism of the effects of heroin in humans," *Psychopharmacology*, 159:351-360 (2002).

Kranzler et al., "Sustained-Release naltrexone for Alcoholsim Treatment: A Preliminary Study," *Alcoholism: Clin. and Exp. Res.*, 22(5):1074-1079 (1998).

Leary, "Drug for Heroin Addiction Is Being Marketed for Treatment of Alcholism," *New York Times*, p. A18, Jan. 18, 1995.

Nath et al., "Buprenorphine Pharmacokinetics: Relative Bioavailability of Sublingual Tablet and Liquid Formulations," *J. Clin. Pharm.*, 39:619-623 (1999).

Nuwayser et al., "Microencapsulation of Contraceptive Steroids," *Proc. 11th Inter. Symp. Control. Rel. Bioactive Mater.*, pp. 71-72 (1984).

Nuwayser and DeRoo, "Microencapsulation with Microfluidized Beds," *Proc. 14th Inter. Symp. Control. Rel. Bioactive Mater.*, 2 pages (1987).

Nuwayser et al., "Sustained Release Injectable Naltrexone Microcapsules," *Proc. Inter Symp. Control. Rel. Bioactive Mater.*, 15:201-202 (1988).

Nuwayser et al., "Sustained Release Injectable Methadone Microcapsules," *Proc. Inter. Symp. Control. Rel. Bioactive Mater.*, 16:83-84 (1989).

Nuwayser et al., "Sustained Release Injectable Naltrexone Microcapsules," *Proc. 52nd Ann. Sci. Meeting*, L. Harris, ed. NIDA Research Monograph 105, 532, (1991).

Nuwayser and Blaskovich, "*In Vivo* Studies of a One Month Injection for Buprenorphine," *Proc. Inter. Symp. Control. Rel. Bioactive Mater.*, 19:168-169 (1992).

Petry et al., "A Comparison of four buprenorphine dosing regimens using open-dosing procedures: is twice-weekly dosing?" *Addiction*, 95(7):1069-1077 (2000).

Petry et al., "Examining the limits of the buprenorphine interdosing interval: daily, every-third-day and every-fifth-day dosing regimens," *Addiction*, 96(6):823-834 (2001).

Przyborowski et al., "Preparation of HSA Microspheres in a One-Step Thermal Denaturation of Protein Aerosol Carried in Gas-Medium," *Eur. J. Nuc. Med.*, 7:71-72 (1982).

Shah et al., "A biodegradable injectable implant for delivering micro and macromolecules using poly(lactic-co-glycolic)acid (PLGA) copolymers," *J. Controlled Release*, 27:139-147 (1993).

Williams et al., "Microencapsulated Local Anesthetics," *Proc. 11th Inter. Symp. Control. Rel. Bioactive Mater.*, pp. 69-70 (1984).

* cited by examiner

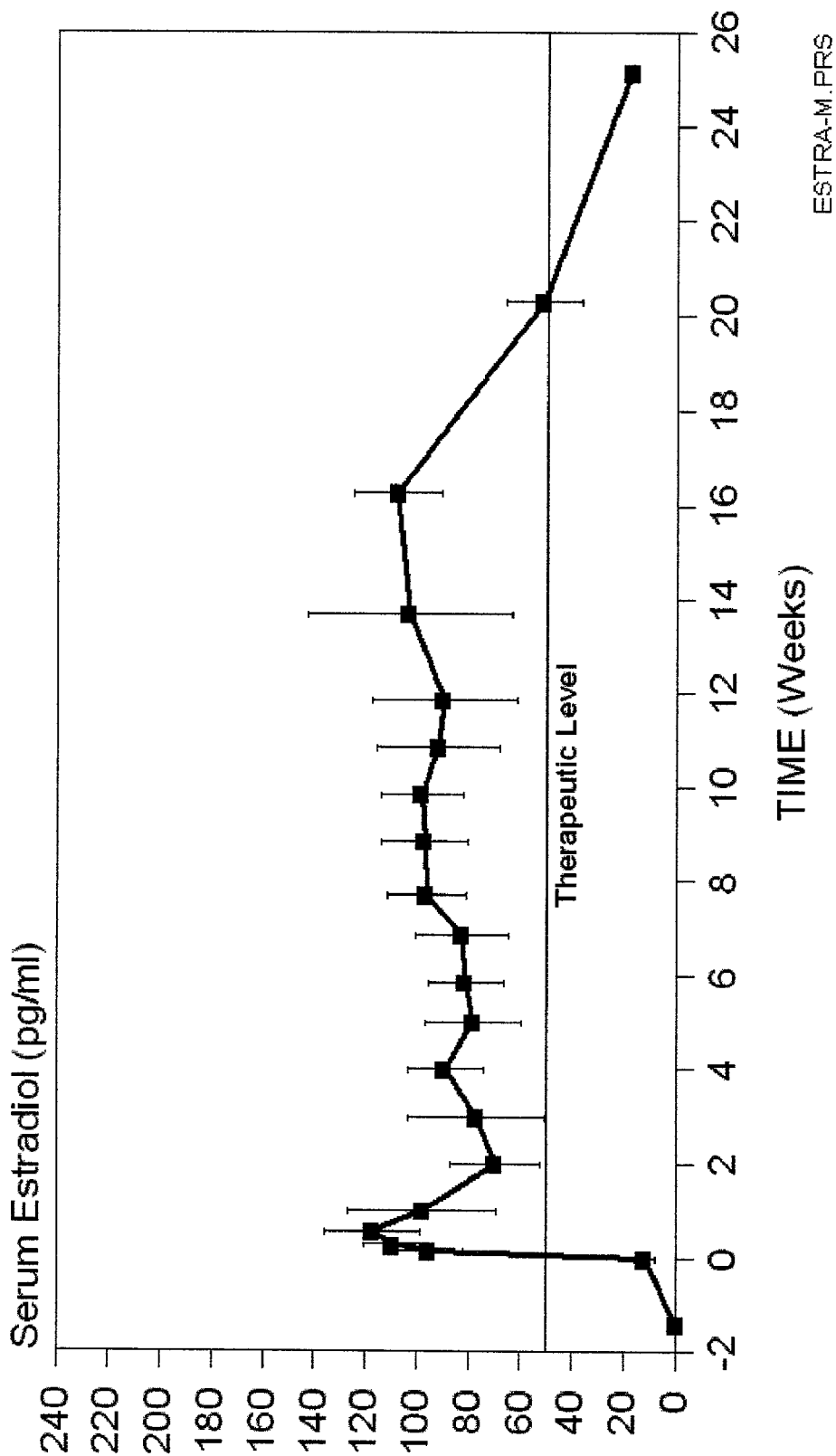
Figure 2. Plasma Level of Beta-Estradiol from Estrel™ Microcapsules in Five Women

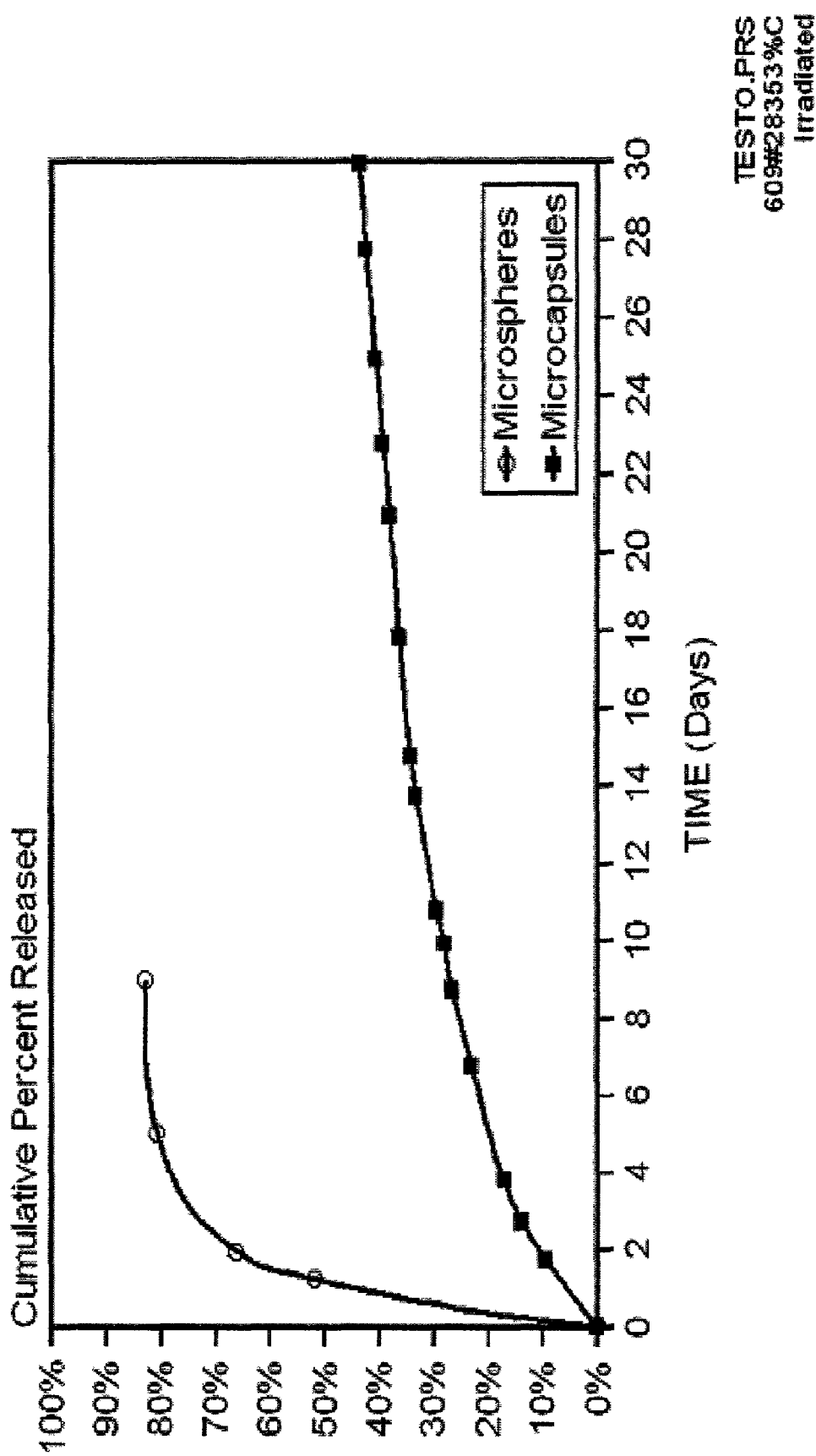

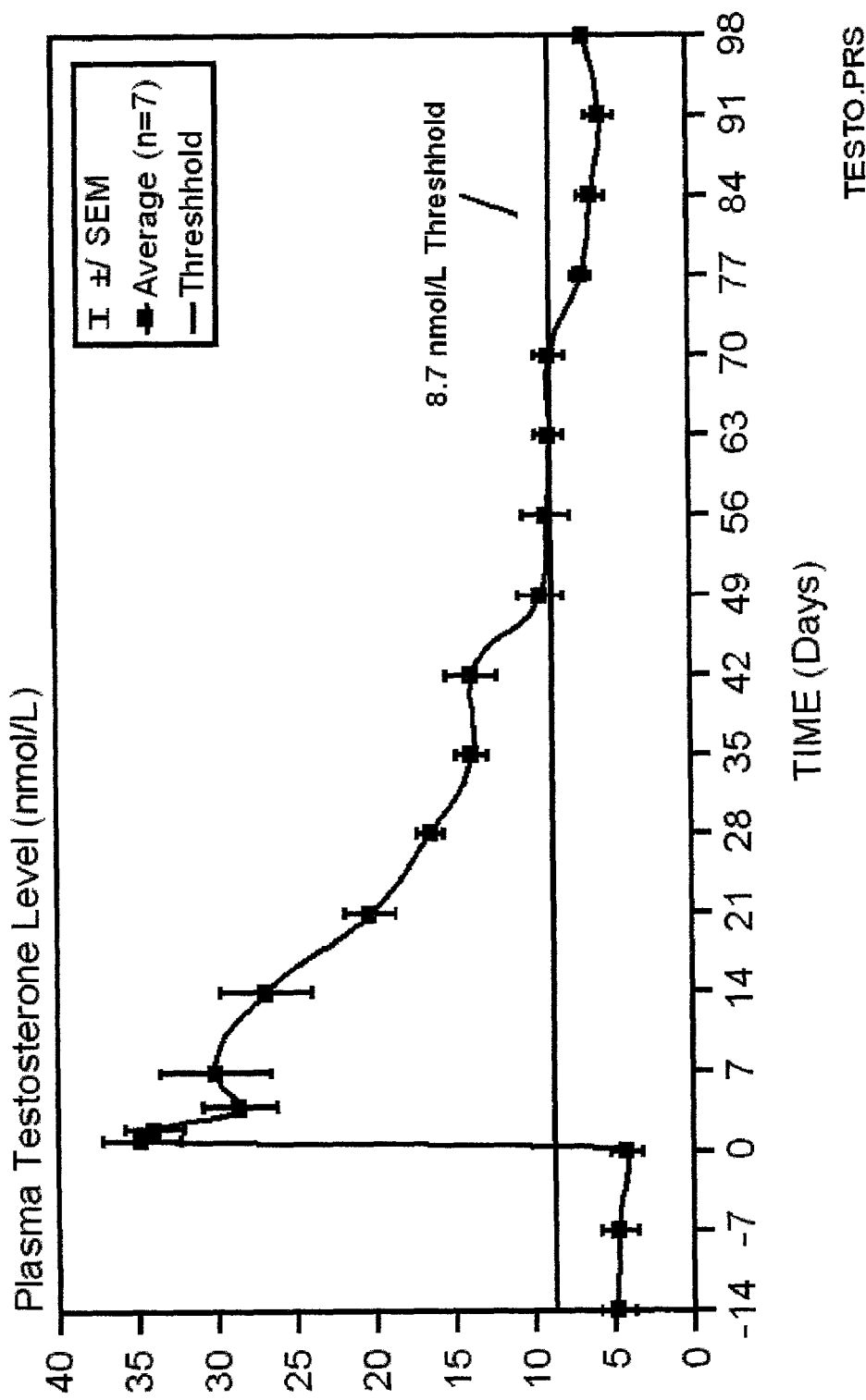

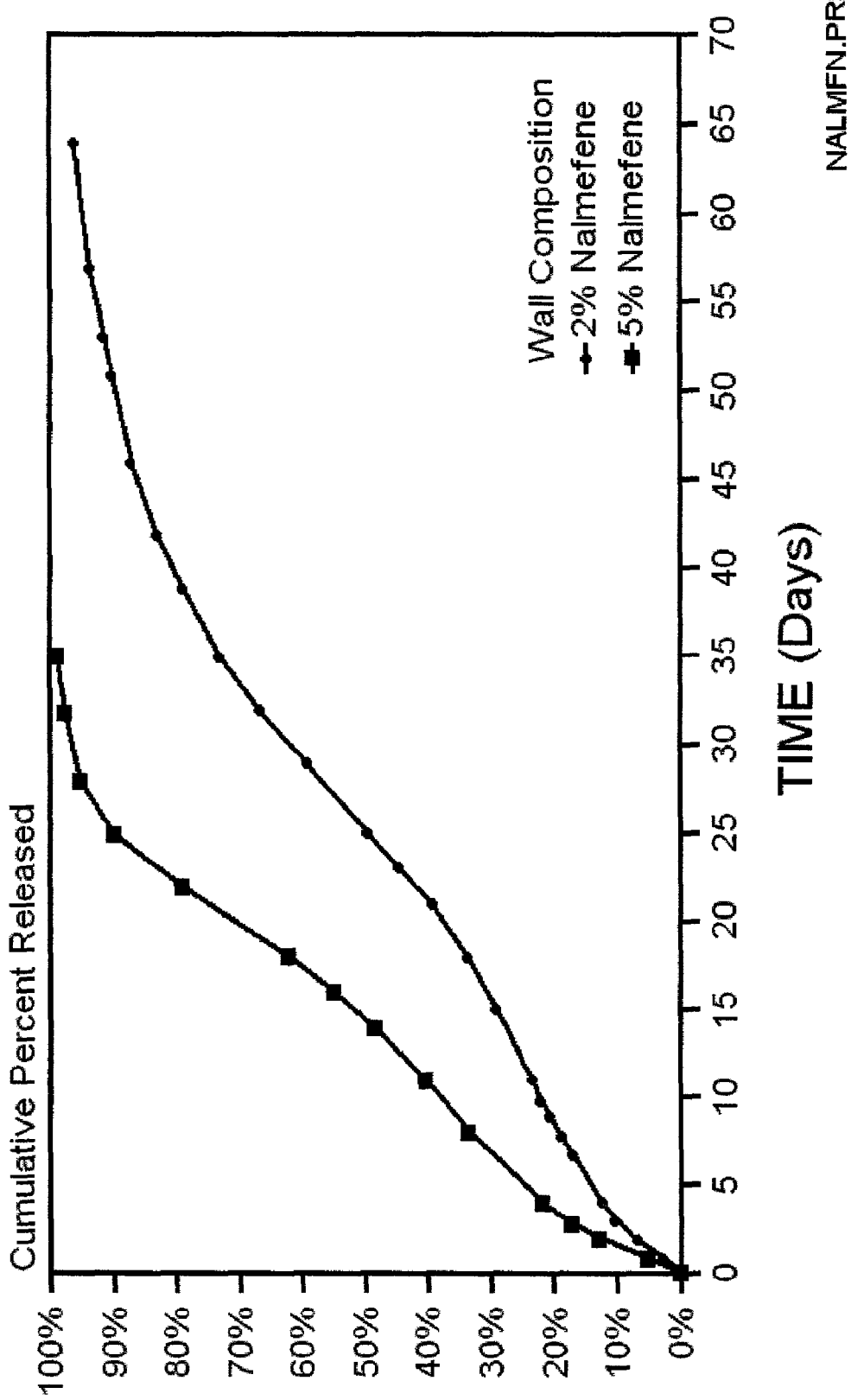

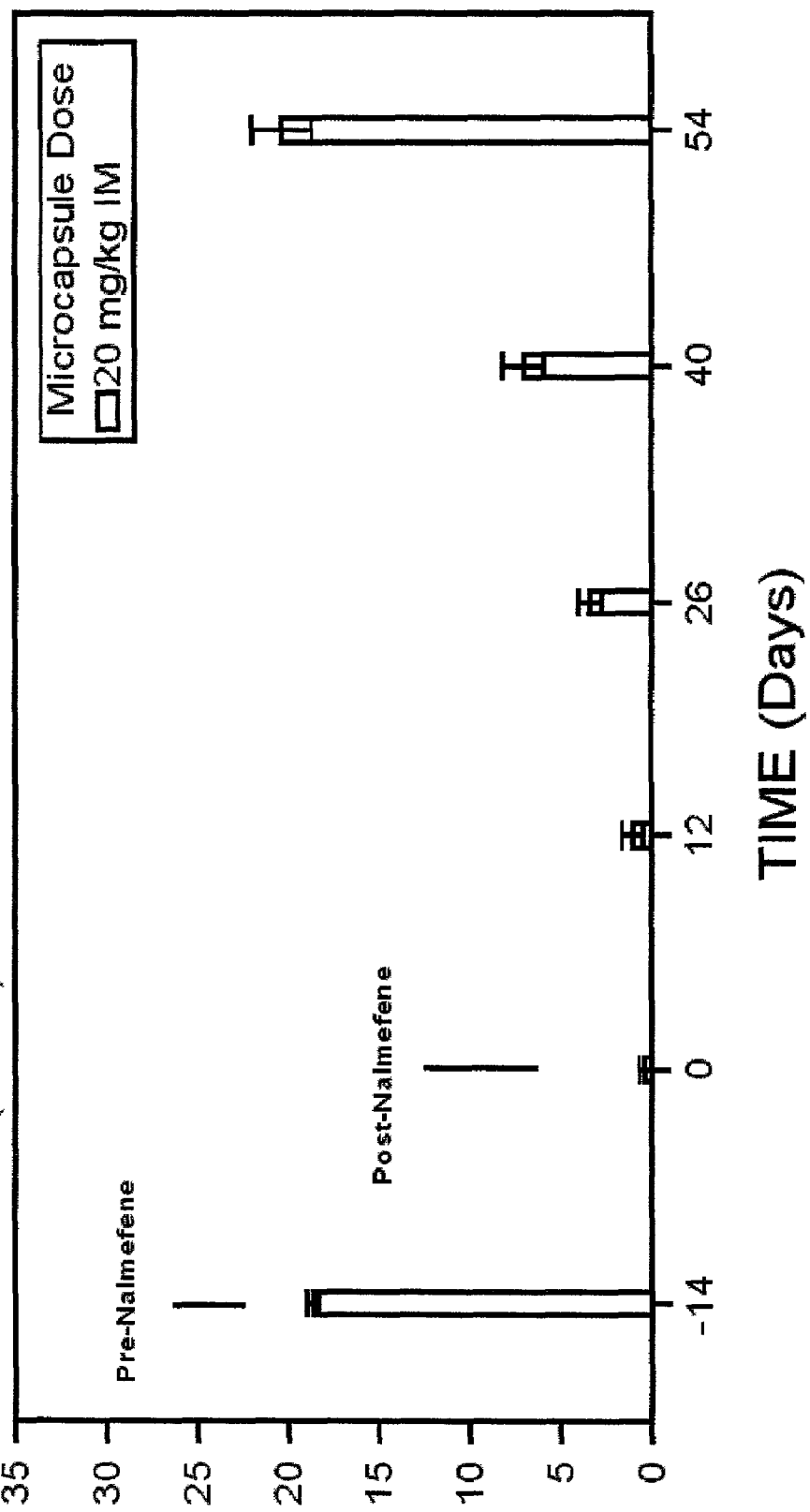

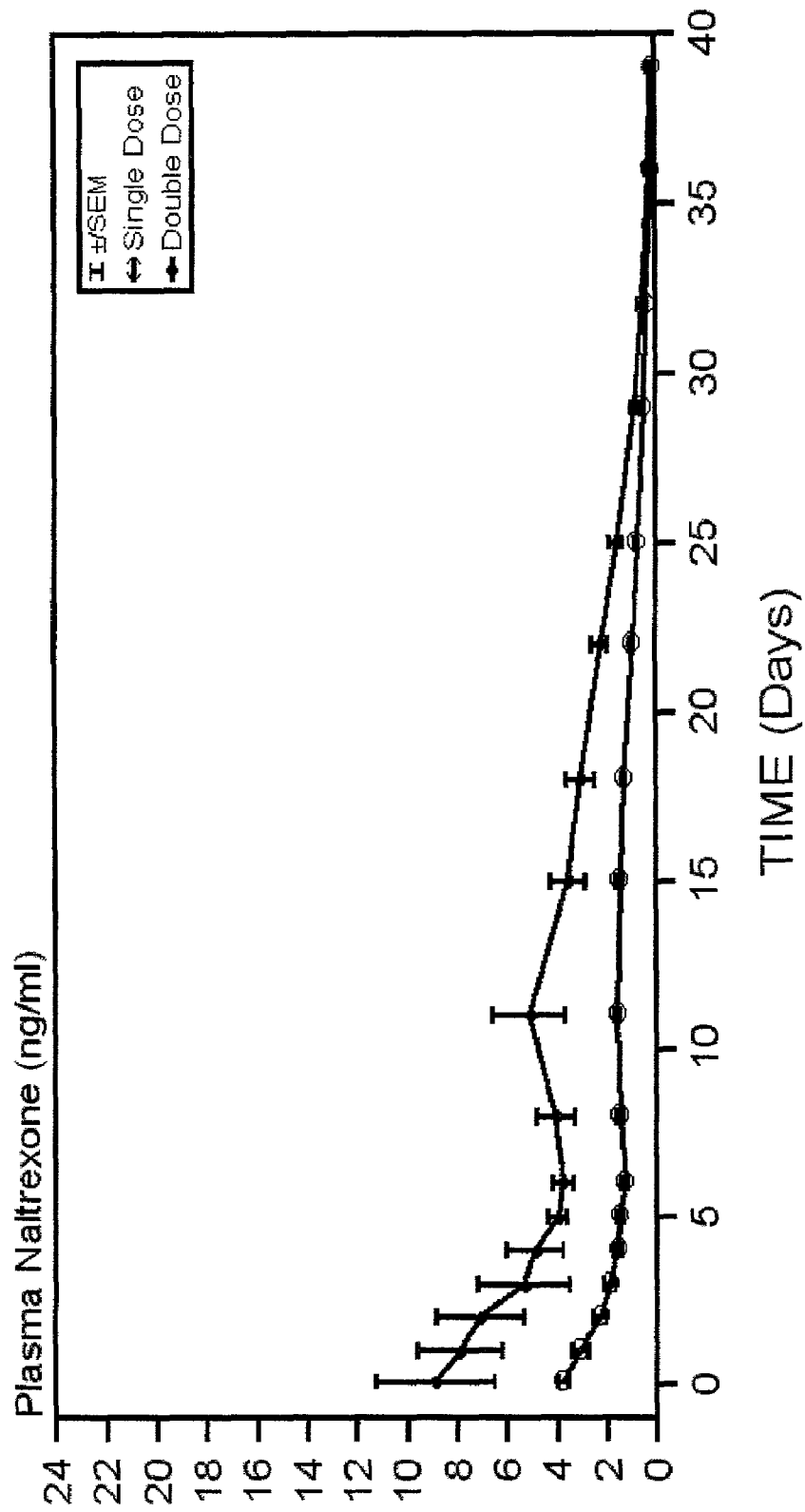
Figure 7. Naltrexone Plasma Level in Six Human Subjects After Single and Double SC Injections of Depotrex™

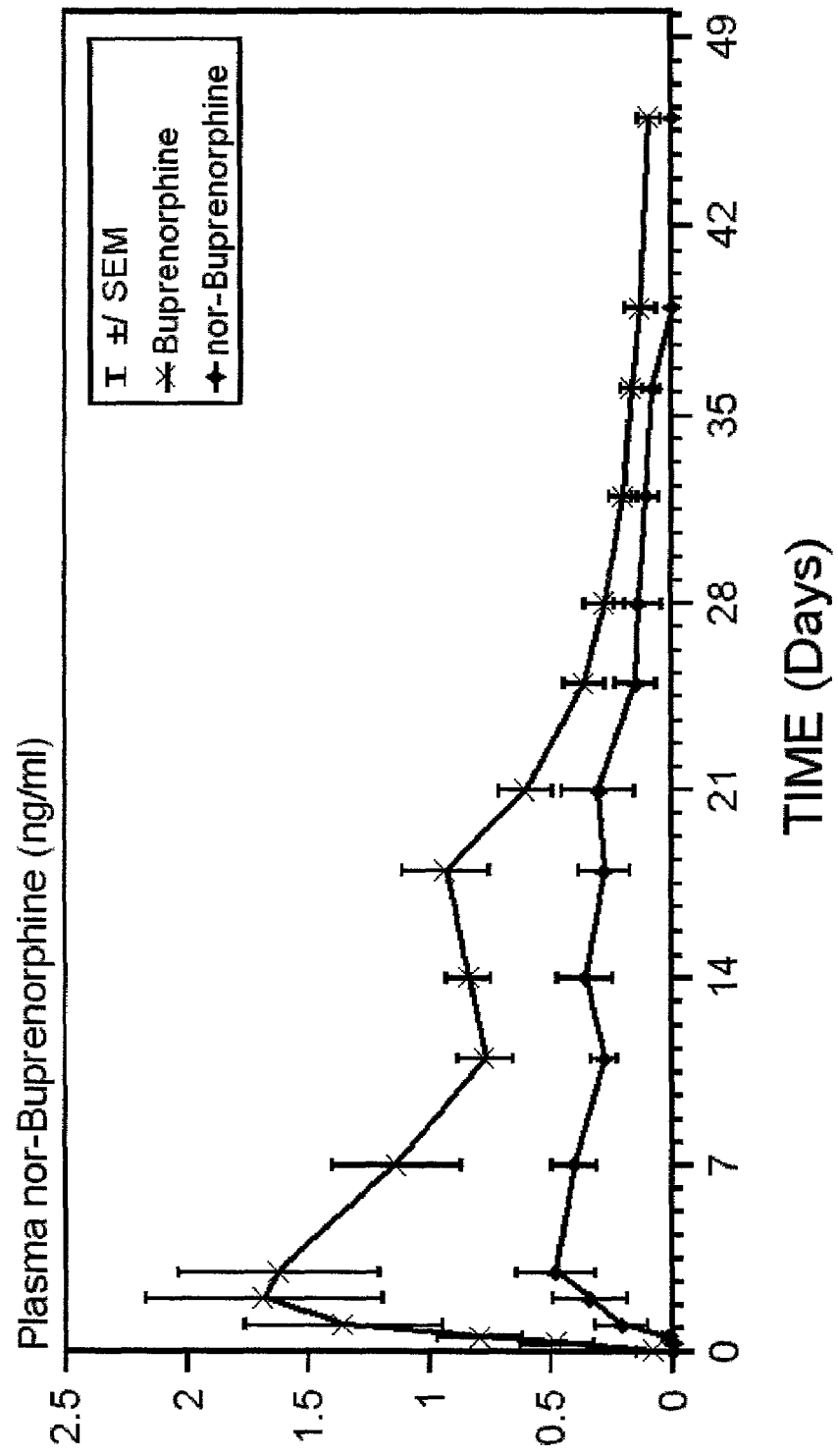

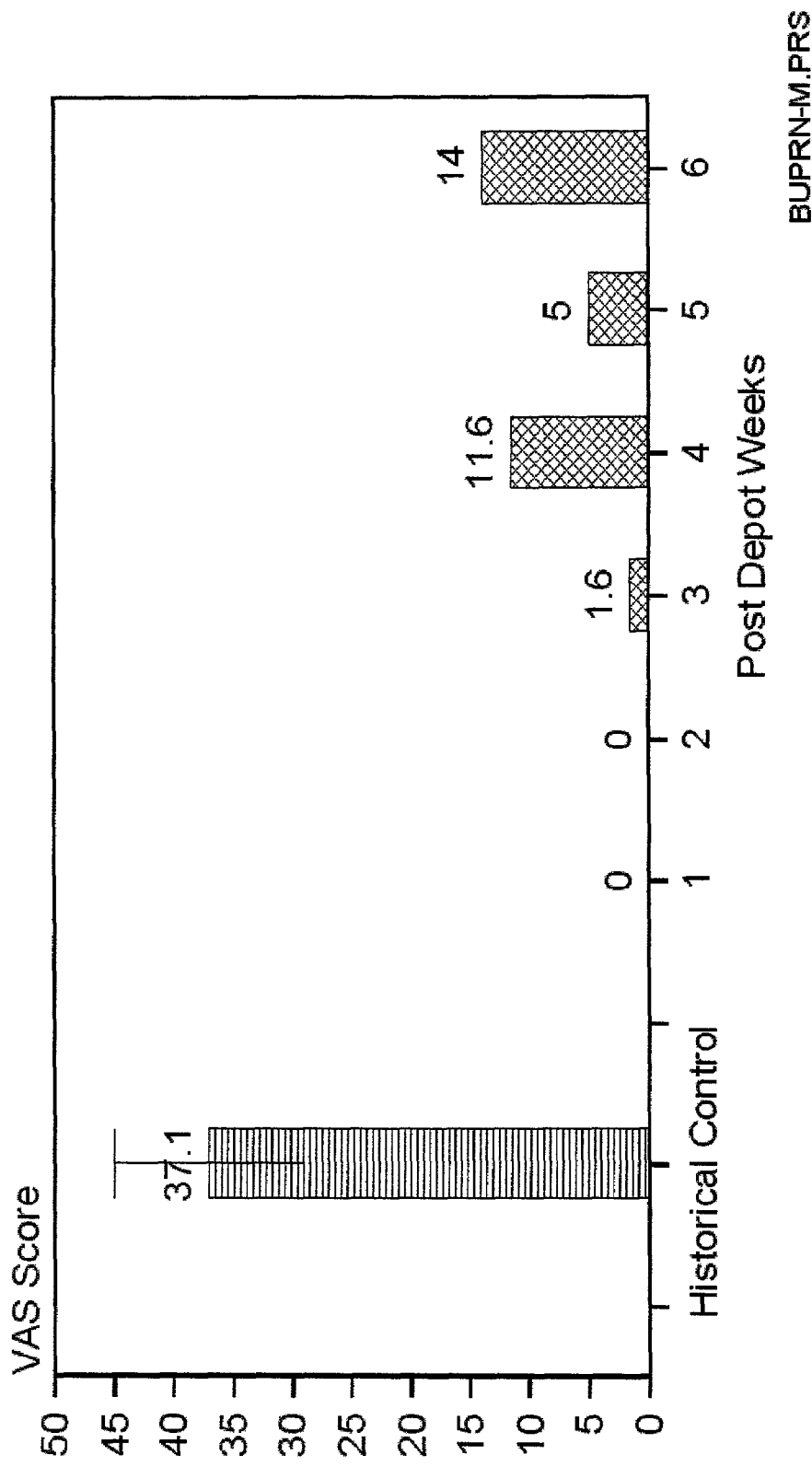
Figure 9. Effect of Norvex™ Depot Buprenorphine SC Injection on VAS Drug Effect in Response to Opioid Challenge in 5 Heroin Addicts

MULTI-LAYERED MICROCAPSULES AND METHOD OF PREPARING SAME

BACKGROUND OF THE INVENTION

1. Field of the Invention

Embodiments of the present invention relate generally to the field of microparticles for the controlled delivery of pharmacologically active agents over a prolonged period of time. In particular, embodiments of the present invention are directed to microparticles having one or more layers or coatings that are capable of delivering one or more pharmacologically active agents either simultaneously or in series over a prolonged period of time, at the same or different release rates. Embodiments of the present invention are further directed to methods for the production of microparticles having a high concentration of active ingredient and a low residual solvent concentration.

2. Description of Related Art

Microparticles, suitable for the controlled release of an active ingredient, such as various drugs, and a process for preparing and using said microparticles, have been described for example, in U.S. Pat. No. 4,568,559, U.S. Pat. No. 4,623,588, and U.S. Pat. No. 5,648,097, all of which are hereby incorporated by reference in their entireties. As disclosed, microparticles are typically comprised of solid composite core material of a uniform dispersion of finely divided active ingredients or solid solution of a drug in a core-forming polymer and include a generally outer wall coating about the composite core material, to provide for the desired controlled or sustained release of the active ingredient from the microparticles. Further, the active ingredient may comprise a dissolved or finely divided, active, drug-type ingredient for the treatment of a mammal and generally the core forming polymers would be comprised of a biodegradable polymer with the outer uniform wall thickness also including a biodegradable polymer, with a size of typically less than about 200 microns to provide for an injectable form for the microparticles.

The particles are typically prepared with varying organic solutions of the active ingredient and the core-forming polymer such as, for example, employing methylene chloride to aid in the solution of the active ingredient and then removing the solvent to provide a dry composite admixture of the active ingredients and the core-forming polymer material. The dry composite admixture so prepared is then pulverized or ground-up and then screened to provide composite core particles of a defined particle size. The ground-up, reduced, and selected drug polymer admixture may then be coated with a film-forming polymer material to form a microcapsule having a generally uniform outer wall coating about the ground-up composite core material used.

In other methods of making microparticles having a core of active ingredient material, a polymer material is dispersed in a solvent and blended with a solution containing an active ingredient to be encapsulated by the polymer. As solvent is withdrawn from the dispersion, e.g., by evaporation or extraction, microparticles of the polymer material form and encapsulate a solution of core active ingredient. See U.S. Pat. Nos. 3,523,906 and 3,737,337. U.S. Pat. No. 3,691,090 describes a process in which a dispersion of a core material in organic solvent is added dropwise to an aqueous buffer, followed by evaporation of the organic solvent to yield microparticles containing a core material. U.S. Pat. No. 3,891,570 describes a process for preparing microspheres or microcapsules in which a solvent is used to dissolve or disperse the polymeric material and is removed by evaporation. U.S. Pat. Nos. 4,389,330 and 4,530,840 describe processes of microencapsulating an active ingredient in which solvent used to dissolve or disperse polymer material is removed in a two-step process involving low pressure evaporation of a portion of the solvent followed by an extraction of the remaining solvent.

Another method of preparing microparticles containing an active ingredient is to use a coacervating agent, such as silicone oil, which promotes polymer material to deposit as droplets of solvent swollen polymer on water droplets containing the active ingredient to be encapsulated. See U.S. Pat. Nos. 4,675,189 and 4,897,268. Other methods of preparing microparticles and microcapsules are disclosed in U.S. Pat. No. 4,542,025 and U.S. Pat. No. 5,407,609.

Conventional methods of microencapsulation use a surfactant at a concentration of greater than 0.1% to stabilize the emulsion formed when the polymer solution (usually dissolved in a solvent such as methylene chloride, ethyl acetate, methyl ethyl ketone, dimethyl sulfoxide or other suitable organic solvent) is combined with an aqueous solution of an active ingredient to be microencapsulated. Furthermore, conventional microparticles of many drugs having active ingredient concentrations, i.e., on the order of 40% to 50% w/v, release their active ingredient content very rapidly and therefore cannot be used for long sustained delivery of the drug since a large portion of the drug is composed of active ingredient. As a result, their duration of activity is short. This occurs especially with drugs that require a high dose for therapeutic efficacy. In order to deliver a sustained dose from these drugs over a maximum period of time, it is essential that the microparticles have a high drug content. Another problem with conventional microparticles is that control of the rate of release of the drug from the microparticles is limited to varying the intrinsic properties of the microparticles such as the size of the microparticles, their drug content or the type of polymer used. The intrinsic methods for controlling the release of the drug are dependent on the properties of the microparticles themselves, and are not always available to the formulator because of limitations in the daily dose of the drug, the physical-chemical properties of the drug, desirable duration of activity, and rate of degradation of the polymer.

Therefore, there is a need to develop methods for controlling the rate of release of the drug that are independent of intrinsic methods. There is also a need to develop microparticles having a high drug content that control the rate of release of the drug into surrounding media. Microparticles prepared by conventional methods are generally more easily damaged by physical force since the majority of the microparticle is comprised of active ingredient and not the polymer which forms the matrix which holds the microparticle together. As a result, microparticles having high drug concentrations and uniform structure from microparticle to microparticle are generally difficult to prepare.

Also, many conventional microcapsules share a common limiting feature in that they are designed to deliver a single active ingredient at a single release rate since existing methods of making microcapsules generally comprise forming a single polymer wall around a core containing a single active ingredient. Therefore, a need exists to develop microcapsules which are capable of delivering one or more active ingredients at the same or different release rates over a prolonged period of time. A further need exists to provide a drug delivery device in the form of a multilayered microcapsule which can be readily and simply designed to provide a specific desired release profile of one or more active ingredients tailored to optimize treatment of a particular disease or condition within a mammal, such as a human. A further need exists to develop therapeutic methods based upon the multilayered microcapsules of the present invention for treating one or more disorders with a single microcapsule design. A still further need exists to develop therapeutic methods based upon the multilayered microcapsules of the present invention for treating a single disorder with a combination of active ingredients, which is commonly referred to as a "cocktail therapy".

An even still further need exists to provide for new and effective microcapsules which avoid at least some of the disadvantages of the prior art microcapsules, and which provide additional advantages of greater uniformity, size and ease in preparation and lower toxic solvent content than the prior art microcapsules.

SUMMARY OF THE INVENTION

Embodiments of the present invention relate to a multi-layered microcapsule for the controlled release within a mammal, including a human, of one or more active ingredients such as drug compounds. The term "microcapsule" as used herein refers to an inner microparticle core also referred to as a "microsphere" which has been encapsulated by one or more layers of a polymer, active ingredient, or polymer/active and/or inactive ingredient composite or mixture, hereinafter referred to generally as "coating layers". The inner microparticle core may or may not include the active ingredient. For the purposes of describing the present invention, the terms "emulsion", "dispersion" and "solution" shall be used as appropriate to refer to a mixture or combination of polymer and/or active medium and a liquid medium, such as a solvent, dispersing, or emulsifying medium. The microcapsules have certain physical characteristics useful for biodegradable delivery systems, including desirable solubilities and porosities for sustained delivery of an active ingredient in a relatively constant manner over periods of days, weeks, months, or years.

According to an alternate embodiment of the present invention, a multilayered microcapsule for the controlled release of one or more active ingredients is provided that includes an inner solid microparticle core, a plurality of active ingredient layers with each active ingredient layer including an active ingredient alone or in combination with a first polymer, and at least one wall layer including a second polymer and being contiguous with an active ingredient layer. Active ingredient layers can be contiguous with each other or they may alternate with wall layers as desired to produce a desired active ingredient release profile into surrounding media.

Alternate embodiments of the present invention are directed to multi-layered microcapsules which are capable of delivering one or more active ingredients either simultaneously or in series over a prolonged period of time at the same or different release rates. Additional embodiments of the present invention are directed to pharmaceutically acceptable formulations which include the microcapsules of the present invention and to methods of treating individuals or preventing conditions in individuals. Still additional embodiments of the present invention relate to novel methods for making a drug-loaded microparticle core and a multi-layered microcapsule.

According to one embodiment of the present invention, the multi-layered microcapsules have one or more active ingredients contained in a single microcapsule. The multi-layered microcapsules are designed to include an inner solid microparticle core which may or may not contain an active ingredient which is then coated with one or more alternating layers of polymer, active ingredient or polymer/active ingredient mixtures to produce a multi-layered microcapsule of the present invention wherein the polymer or active ingredient in each layer may be the same or different or have the same or different concentration of the polymer or active ingredient in other layers.

Optionally and preferably, the microcapsule includes an outer wall layer as the exterior layer of the microcapsule which is contiguous with an active ingredient layer. The wall layer is formed from a biodegradable polymer of sufficient thickness and composition to control the rate of sustained release of active ingredient from the microcapsule. The outer wall layer may, for example, include a water-leachable material such as a drug or even a plasticizer which is leached out during use to provide pores in the outer wall layer to increase the rate of release of active ingredient in the interior of the microcapsule. It is envisioned that one or more wall layers, for example, 2, 3, 4, or 5 wall layers, may also be internal to the microcapsule and may separate active ingredient containing layers. Typically, where the polymer is a biodegradable polymer, the polymer would comprise a homo- or co-polymer of glycolide or lactide monomer.

Embodiments of the present invention further include methods of making microparticles, which can be used as a core in the multi-layered microcapsule, having a high active ingredient concentration and a low concentration of residual solvent used in preparing the microparticles. More particularly, methods are disclosed herein for preparing a microparticle containing an active ingredient wherein the active ingredient constitutes from 0.1 to 80% or more by weight of the microparticle. In the methods of the present invention a microparticle core is prepared by any of several well known methods such as casting and grinding, emulsification and solvent evaporation, spraying, palletizing, spinning or rolling, etc. The core microparticle may or may not contain one or more active ingredients or drugs or biologically active ingredients. In the methods of the present invention, an emulsion is formed at room temperature by mixing an organic phase, such as of a solubilized or dispersed polymer and an active ingredient, with an aqueous phase, such as water or an aqueous buffer. During the formation of microparticles of the polymer and active ingredient, the temperature of the emulsion is raised from room temperature, such as according to a preselected temperature gradient, to a preselected temperature depending on the polymer, active ingredient and solvent selected to form the microparticles. The temperature of the emulsion is increased with time in a manner to allow the solvent to slowly migrate out of the core microparticles leaving only low physiologically acceptable residual levels and without significantly disturbing the integrity of microparticle shape or structure, or microparticle drug delivery, drug content or other properties Embodiments of the present invention also include the process of preparing a multi-layered microcapsule for the sustained or controlled release of one or more active ingredients, which process comprises coating, such as by spray coating, one or more coating layers, preferably generally uniform in dimension, in sequence about a solid microparticle core material, wherein the coating layers comprise one or more biodegradable polymers, one or more active ingredients or a mixture of one or more active ingredients and one or more biodegradable polymers, and then recovering a multi-layered microcapsule. Each coating layer may be an active ingredient containing layer having an active ingredient alone or in combination with a polymer or it may be a wall layer of pure polymer.

Embodiments of the present invention also include using the microcapsules for the sustained or controlled release of active ingredient from the microcapsule over a defined time period into surrounding media, such as in a mammal. Useful time periods include one day, one week, one month, several months, one year or longer. The microcapsules of the invention may be administered and placed into the environment to provide for the controlled release of active ingredient into the environment by a variety of techniques, for example an effective amount of the microcapsules may be administered to the animal orally, intranasally or parenterally e.g., intravenously, intramuscularly, subcutaneously, intraperitoneally, or the like.

It is accordingly an object of the present invention to provide microcapsules having multiple layers of polymer, active ingredient or polymer/active ingredient admixture, (i.e. 2, 3, 4, 5, 6, 7, 8, 9, 10 or more layers) which are biocompatable and biodegradable and which can be used in a microcapsule delivery system. It is a further object of the present invention to provide methods of making microparticles having a high concentration of active ingredient and a low concentration of residual solvent. It is a further object of the present invention to provide methods for the preparation of an active ingredient delivery system capable of delivering one or more active ingredients in a controlled fashion. It is a still further object of the present invention to provide methods of therapeutically treating individuals by using a microcapsule delivery system capable of delivering one or more active ingredients as a treatment for or prevention of certain disorders. Other objects, features or advantages of the present invention will become apparent from the following description taken in conjunction with the accompanying drawings.

BRIEF DESCRIPTION OF THE DRAWINGS

In the course of the detailed description of certain preferred embodiments to follow, reference will be made to the attached drawings, in which.

FIG. 2 is a graphical representation of the blood level of estradiol hormone drug in five post-menopausal women from one embodiment of the multilayerd microcapsule of the present invention. The core of this microcapsule is composed of a polymer microsphere. On top of this core is applied a layer of a mixture of polymer and estradiol hormone using the coating apparatus described in FIG. 1. Finally, a layer of polymer is applied to seal the hormone/polymer layer and to control the rate of release of the hormone from the multilayer microcapsule.

FIG. 3 is a graphical representation of the in vitro release of testosterone drug from microspheres and microcapsules. The graph shows the significant increase in the duration of release from the microcapsules compared to the microspheres. The microcapsules represent another embodiment of the present invention.

FIG. 4 is a graphical representation of the blood level of testosterone drug in seven hypogonadal men from the testosterone containing microcapsules.

FIG. 5 is a graphical representation of the in vitro release of the opioid and alcohol antagonistic drug nalmefene from another embodiment of the multilayered microcapsules of the present invention.

FIG. 6 is a graphical representation of the effect of morphine injection challenge on the overt behavioral signs of morphine in monkeys following nalmefene microcapsule injection. The monkeys were challenged with morphine sulfate over a period of 5 observation sessions (observation). Scoring continued at approximately bi-weekly intervals for 8 weeks.

FIG. 7 is a graphical representation of the blood level of the opioid antagonist drug naltrexone in twelve heroin addicts from one embodiment of the microcapsules of the present invention.

FIG. 8 is a graphic representation of the blood level of buprenorphine in heroin addicts given a single depot dose of microcapsules.

FIG. 9 is a graphic representation of the effect of a single injection of microcapsules containing 58 mg of Buprenorphine on visual analog scaling (VAS) drug effect in response to opioid challenge in five heroin addicts.

DETAILED DESCRIPTION OF CERTAIN PREFERRED EMBODIMENTS

Figure 1:
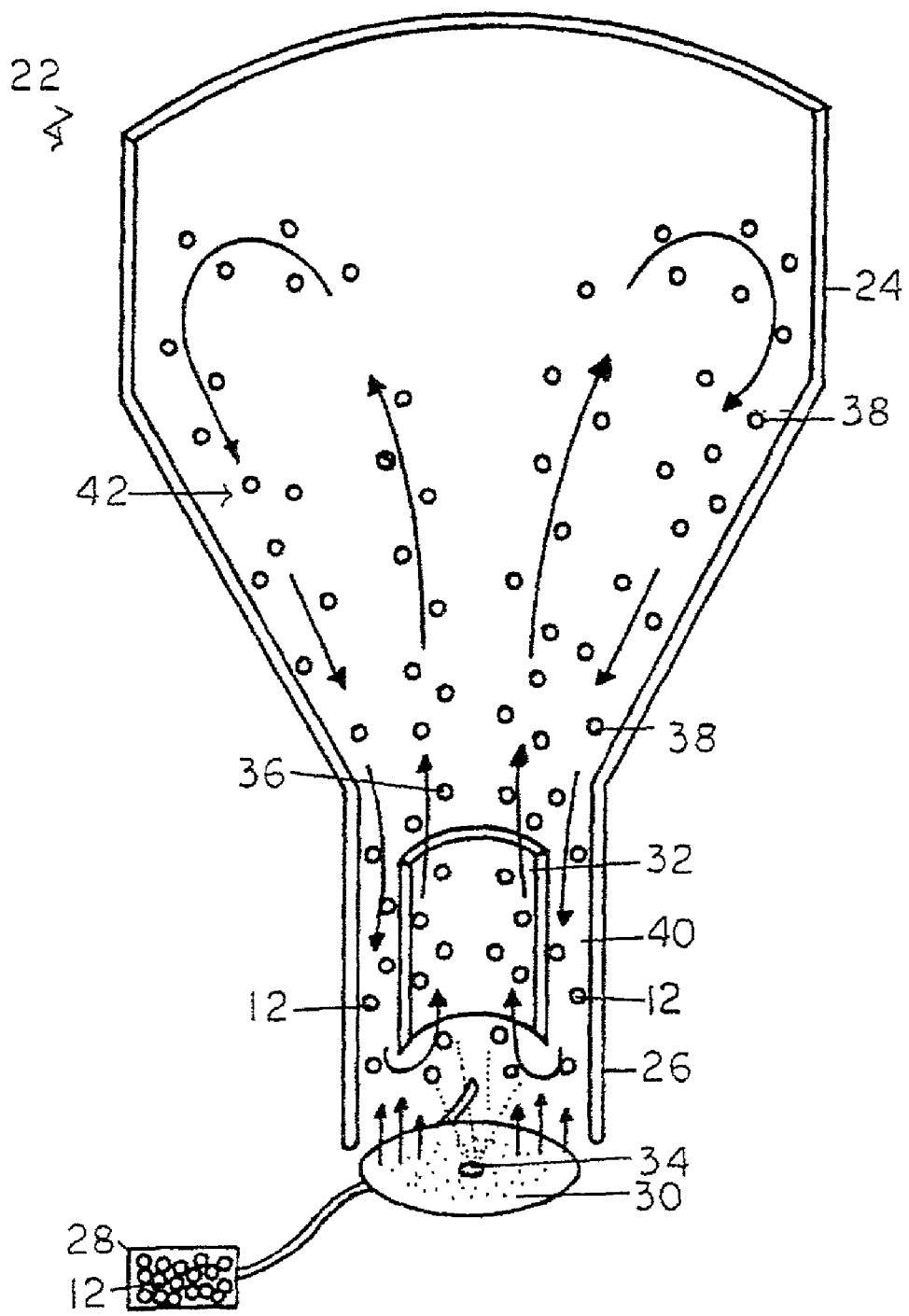
FIG. 1 is a schematic illustrated diagram of a fluidized bed air suspension coating apparatus and process for the production of the microcapsules of the invention.

The principles of the present invention may be applied with particular advantage to provide a novel multi-layered microcapsule design that is capable of delivering a single active ingredient according to one or more controlled release rates if desired, or several active ingredients at one or more controlled release rates all from within a single microcapsule. The microcapsules can be tailored in any layering configuration to achieve delivery of one or more active ingredients for a period of days to weeks to months to years through a single parenteral injection. By pre-selecting a multilayered-microcapsule design, one may tailor a long-term controlled release profile for a variety of active ingredients in a single microcapsule to treat or otherwise prevent a variety of diseases or conditions.

According to the teachings of the present invention, the microcapsule has an inner microparticle core material having a plurality of coating layers about the microparticle core. Surrounding the microparticle core are one or more layers of a polymer (acting as a membrane or wall which controls the rate of release of active ingredient from the microcapsule into a desired environment), an active ingredient, a plasticizer, other additive or a polymer/active ingredient mixture. The core may be composed of pure polymer, an active ingredient or a polymer plus active ingredient. The core particle can also be referred to as a "microsphere" which generally refers to microparticles that do not include one or more coating layers. The core could be composed of milled cast particles, microsphere particles, pelletized particles, fluidized particles or other kinds of particles prepared by methods known in the art. The polymers in each polymer containing layer may be the same or different or may be a mixture of one or more polymers. Likewise, the active ingredient in each active ingredient containing layer may be the same or different or may be a mixture of one or more active ingredients. According to one embodiment, the microcapsule includes a single active ingredient contained in different layers of the microcapsule having different polymers that biodegrade at different rates, thereby providing a release rate for the active ingredient that varies over time according to a desired release profile. According to an alternate embodiment, the microcapsule includes one or more polymer wall layers separating active ingredient-containing layers which differ in the concentration of the active ingredient, for example with declining concentrations extending outwardly from an inner layer. Alternatively, the microcapsule layers contain different polymers and different active ingredients to provide for a sustained and controlled release of a combination of active ingredients according to a desired release profile.

Useful microparticle cores are generally prepared by dissolving a polymer material in a solvent and forming a solvent-in-water emulsion and then evaporating the solvent to form a plurality of suspended solid polymer microparticles which are then recovered. If desired, the microparticle cores may be loaded with an active ingredient which is included in the solvent-water emulsion and becomes incorporated into the microparticle or is otherwise loaded according to standard methods. Alternately, the microparticle cores can be prepared by dissolving the polymer or the polymer and the drug in a solvent and evaporating the solvent. The dried casting of polymer or polymer drug mixture is then milled to the desired size range for coating. The coating layers are generally applied by forming a solution or an emulsion of a polymer and an active ingredient, such as a drug, and then spray coating the solution or emulsion onto the microparticle core according to known fluidized bed air suspension technology. According to this method, the microparticles are first suspended in a moving airstream. The polymer-drug solution or emulsion is then sprayed into the air stream in a manner to coat the microparticle core with the polymer-drug solution or emulsion, i.e., to form a coating layer about the microparticle core. The coated microparticles are then allowed to harden and are then recycled back through the airstream for another application of the drug-polymer emulsion. The coated microparticles are continually recycled through the airstream until a desired thickness of the coating layer is formed. The suspension and spraying process is then repeated with a next desired coating composition of polymer, active ingredient or polymer/active ingredient mixture which may be the same or different from the preceding coating composition. Preferably, the microcapsule may then be coated in the manner described with an outer polymer membrane or other rate-limiting wall.

Preferably, the microcapsules of the present invention are characterized as being substantially uniform in shape, and preferably substantially spherical. Due to their consistent uniform shape and/or smooth surface, the microcapsules of the present invention are less prone to clogging and advantageously provide smooth flow characteristics during delivery from a syringe needle, which is a significant injection performance advantage. The smooth flow characteristics enable a greater concentration of microparticles to be injected and therefore enable the delivery of a greater amount of active ingredient per injection. In the practice of the present invention, an injectable formulation is made by mixing a desired amount of the microcapsules of the present invention with a suitable suspending medium to produce a suspension. A desired volume of the suspension is then drawn into a syringe and injected into a patient.

Polymers useful in the preparation of the microcapsules of the present invention include those that biodegrade when placed in an aqueous environment, such as within a mammal, including a human. A biodegradable polymer is one which is non-toxic and is gradually broken down or adsorbed in the body of an individual into which the polymer is placed. Biodegradable polymers are preferably non-sensitizing and do not elicit an immune response when administered to an individual, thereby permitting, if necessary, additional administrations to the same individual of the microcapsules containing the polymers.

Certain useful biodegradable polymers include those derived from condensation of α-hydroxycarboxylic acids and related lactones which form aliphatic polyesters, including homo or copolymers of mandelic acid, D or L optically active forms or DL optically inactive forms of polylactides (PLA), polyglycolides, polylactide-co-glycolides (PLA-PGA), polycaprolactones, polyhydroxybutyrates, and polyhydroxyvalerates. Other biodegradable polymers include polycarbonates, polyanhydrides, polyorthoesters, polypeptides, polyacetals, polymandelic acid, polymaleamides, polysaccharides, polyesteramides, and the like, as well as copolymers, terpolymers or mixtures of such materials. Other innocuous biodegradable polymers known to those of ordinary skill in the art having the same or similar physical and chemical characteristics as the specifically mentioned biodegradable polymers are also useful in microcapsules of the present invention. In a preferred embodiment, the polymers biodegrade in the course of a few weeks to a few months to a few years. The preferred materials include polymers of lactic acid and glycolic acid and co-polymers of poly-l-lactide co-glycolide in a range between 40:60 and 95:5 co-polymer ratios, respectively and prepared from the L- or DL isomers of the polymer in a wide range of molecular weights.

Useful solvents within the scope of the present invention are those which are capable of dissolving the selected biodegradable polymer and forming a solution and generally include organic liquids. Water immiscible solvents are generally used for preparing the core by the emulsion technique. Both water miscible and water immiscible solvents can be used for applying the coating layers. The solvents include halogenated aliphatic hydrocarbons, aromatic hydrocarbon compounds, halogenated aromatic hydrocarbon compounds, cyclic ethers, alcohols, ketones, esters and the like. Suitable solvents include acetone, chloroform, methylchloroform, methylene chloride, methyl ethyl ketone, oleic acid, caprolactam, dimethyl sulfoxide, tetrahydrofuran, glycofurol, hexafluoroisopropanol, hexafluoroacetone, nitromethane, dibutyl esters, ethyl acetate, methyl acetate, and the like and mixtures of these solvents with each other and/or with water. Preferred solvents include ethyl acetate, acetone, dimethyl sulfoxide, methyl ethyl ketone and methylene chloride.

A wide variety of active ingredients may be employed in the microcapsules of the present invention, the selection of the active ingredient being one whose release is desired to be controlled or sustained in a particular environment and may include, and not be limited to, such materials as fertilizers, based on a soil-type environment, or more particularly, physiologically or pharmacologically active substances that act locally or systemically in the body such as drugs or other biologically active agents. Representative drugs and biologically active agents to be used with the microcapsules of the present invention include, without limitation, proteins, peptides, amino acids, enzymes, hormonally active agents, opioid drug agonists, opioid drug antagonists, peptide drugs, protein drugs, desensitizing agents, antigens, vaccines, anti-infectives, antibiotics, antimicrobials, antiallergenics, steroidal anti-inflammatory agents, antipsychotics, decongestants, miotics, anti-cholinergics, sympathomimetics, sedatives, hypnotics, psychic energizers, tranquilizers, androgenic steroids, estrogens, progestational agents, humoral agents, prostaglandins, analgesics, antispasmodics, antimalarials, antihistamines, cardioactive agents, non-steroidal anti-inflammatory agents, antiparkinsonian agents, antihypertensive agents, β-adrenergic blocking agents, nutritional agents, and the benzophenanthridine alkaloids. To those skilled in the art, other drugs or biologically active agents that can be released in an aqueous environment can be utilized in the described delivery systems. Also, various forms of the drugs or biologically active agents may be used. These include, without limitation, forms such as uncharged molecules, molecular complexes, salts, ethers, esters, amides, etc., which are biologically activated when injected into the body. Specific active ingredients envisioned to have useful therapeutic results as delivered by the microcapsules of the present invention include buprenorphine, methadone, naltrexone, nalmefene, progesterone, testosterone, norethindrone, levonorgestrel, estradiol, povidone iodine, thiothixene, cetylpyridinium chloride, lidocaine, bupivacaine, etidocaine, sodium fluoride, sodium ascorbate, tyrosine, cholesterol, and TBHQ, clonazepam, lorazepam, LHRH, growth hormone, BChE, etc.

The amount of active ingredient incorporated into the microcapsules depends upon the polymer used, the desired release profile, the concentration of active ingredient required for a biological effect, and the length of time that the active ingredient has to be released for treatment. The lower limit of active ingredient incorporated into the microcapsules is dependent simply upon the activity of the active ingredient and the length of time needed for treatment. Preferably, a sufficient amount of the active ingredient is spray coated into each desired layer forming the microcapsules so as to produce a total amount sufficient to render the microcapsules therapeutically useful.

Microcapsules of various sizes may be employed based upon the teachings of the present invention. For example, microcapsules having a diameter of less than 1000 microns are useful in the practice of the present invention. Even more desirable are microcapsules having a diameter of between 5 to 500 microns. Microcapsules of less than 1000 microns in diameter are preferred for oral administration in a drug-polymer reactive capsule, and generally microcapsules of less than 200 microns are preferred where the drug-polymer microcapsule is to be administered in a suspension as an injectable material.

The following examples are set forth as representative of the present invention. These examples are not to be construed as limiting the scope of the invention as these and other equivalent embodiments will be apparent in view of the present disclosure, figures, and accompanying claims.

EXAMPLE I

Preparation of a Polymer Microparticle Core

Generally, the microparticle cores are prepared according to a solvent-dispersion evaporation technique, such as described in U.S. Pat. Nos. 4,389,330 and 4,530,840, hereby incorporated by reference in their entirety, which leads to essentially spheroidal microparticles having a uniform surface. Briefly, the polymer is mixed with an organic medium or solvent such as methylene chloride, ethyl acetate, or dimethylsulfoxide and combinations thereof to form a solution. The solution is then emulsified into an aqueous or nonsolvent medium for the polymer containing a surfactant, such as polyvinyl alcohol to form essentially spheroidal microparticles. When the solvent is evaporated the solid microparticles to be used as cores in the multi-layered microcapsules, are then recovered. The recovered microparticle cores are then dried at elevated temperatures, for example about 60 to 90 degrees centigrade, for several hours in a moving air stream to evaporate or otherwise remove solvent from the microparticle. In this manner, the residual level of solvent employed, e.g., methylene chloride, is at a physiologically acceptable level for humans depending on the solvent. The microparticle cores are then subsequently subjected to spray coating of one or more coating layers thereon in a moving airstream in a fluidized air bed.

The microparticle core is described in one particular embodiment as a solid polymer core material, such as, for example, a biodegradable or biocompatible, pharmaceutically acceptable polymer, where the microparticle core is to be employed in a drug-containing microcapsule. The microparticle core may comprise a wide variety of polymeric or non-polymeric materials. Preferably, the microparticle core is essentially spheroidal in nature having a smooth, uniform surface and forms a particularly effective and advantageous base for the application of one or more of the desired coating layers. For example, the microparticle core may comprise finely divided inert particles, as well as polymer particles prepared by a formative evaporation spray technique. The microparticle core may be comprised of the polymer or another material, such as an inert material, to form support for the coating layers. Generally, the microparticle core material may vary in particle size, but generally should be substantially uniform in particle size and range from about as low as 5 microns to as high as 500 microns or higher depending on the ultimate size of the microcapsules, but typically would range from about 20 to 150 microns, and more preferably within the range of 40 to 60 microns.

Some useful solvents within the scope of the present invention, such as methylene chloride, have a tendency to be retained by some polymers and some drugs very tenaciously, and thus their removal from a drug containing microparticle core becomes quite difficult as damage to the microparticle core or drug contained therein often occurs from heating at high temperatures. According to the teachings of the present invention, the preparation of a solid polymer microparticle core absent an active ingredient for later encapsulation is advantageous since preferred solvents like methylene chloride can be used because the solid polymer microparticle core can be subjected to temperatures and conditions which remove all but a very minor amount of residual solvent. Where active ingredients are absent from a microparticle core to be later encapsulated, the core may be heated to drive out substantial quantities of the methylene chloride, so that in the resulting microcapsules, there is a very low level of methylene chloride or other solvents. This advantageously allows administration of the microcapsules of the present invention to the chronic user without danger of exposure to high levels of residual solvent.

A microparticle core absent an active ingredient is made in detail as follows: Thirty grams Poly-DL-lactide-co-glycolide 85:15 polymer is dissolved in 180 ml of methylene chloride. Next, 250 ml of a 10% solution of polyvinyl alcohol is mixed with 2.25 liters of distilled water, and stirred at 1,100 rpm with a 6-blade stainless steel propeller. The polymer solution is poured in through a long-stemmed funnel, which is broken into spherical droplets by the propeller. Five minutes later the propeller speed is reduced to 400 rpm, and the mixture stirred for 17–20 hours to allow the spheres to harden by evaporation of the methylene chloride. The temperature is slowly raised to 80° C. to drive off the residual methylene chloride. After cooling to below 30° C., the microspheres are allowed to settle, then the supernatant is decanted, and the microspheres are collected on 8" stainless steel sieves and washed with distilled water. The microspheres are collected and dried at room temperature for at least 48 hours. The above procedure is repeated until a sufficient amount of polymer placebo microspheres has been prepared. Polymer core microspheres were assayed for residual solvent content. The average value obtained for 5 microsphere runs was 6.9 micrograms per milligram or 0.69%.

EXAMPLE II

Preparation of a Microparticle Core Containing an Active Ingredient

A microparticle core containing an active ingredient is prepared according to the method described in Example I in which an active ingredient is included in the solution prior to formation of the microparticle. Alternatively, other methods are known in the art for preparing a microparticle containing an active ingredient that is useful in preparing the multilayered-microcapsules of the present invention.

A microparticle having a high concentration of active ingredient and a low, physiologically acceptable level of residual solvent that is useful as a core material for a multi-layered microcapsule, may if desired be generally prepared as follows. A polymer and active ingredient are dispersed or dissolved in a solvent, which is immiscible with water or aqueous buffers. The amount of solvent used to disperse or dissolve the polymer and active ingredient is kept to a minimum to minimize the amount of residual solvent retained in the microparticles. At room temperature, the solution of polymer and active ingredient is then slowly added to an aqueous phase, which is then stirred to form an emulsion. Optionally, a surfactant such as polyvinyl alcohol may be added to the aqueous phase. Preferably, the concentration of the surfactant in the aqueous phase is from 0.1 to 10% w/v. The temperature of the emulsion is then increased to approximately 45° C. by a programmable heating unit until the temperature reaches approximately 45° C. at which point the heating is stopped. Preferably, the emulsion is heated at a constant rate of approximately 10° C. per hour until the temperature reaches approximately 45° C. at which point the heating is stopped. More preferably, the emulsion is heated at a slower rate of approximately 1.0–2.0° C. per hour until the temperature of the emulsion reaches approximately 45° C. While not wishing to be bound to any scientific theory, the increase in temperature generally and the slow constant rate of heating in particular is believed to promote the more effective and orderly diffusion and release of solvent molecules from the microparticles as they form without cracking or otherwise damaging the microparticle structure.

After the temperature of the emulsion reaches approximately 45° C., the heating is discontinued, but stirring is maintained to continue to maximize hardening of the microparticles. Preferably, stirring is continued until the temperature of the emulsion decreases below 30° C. The microparticles are then collected with a sieve, washed with water or aqueous buffer and then air dried. The microparticles are present in a range of diameter sizes with greater than 80% of the microparticles being present in the range of 25 to 150 microns in diameter.

A sample of the microparticles is analyzed by high pressure liquid chromatography according to methods well known to those skilled in then art to determine the content of the active ingredient as a percent by weight of the microparticles and also by gas chromatography to determine the amount of solvent remaining as a residue within the microparticles. Preferably, the microparticles contain greater than 50% active ingredient by weight, and more preferably greater than 60%, 70%, 75%, 80%, 85% or greater active ingredient by weight of the microparticles.

Preparation of 86% (w/w) Progesterone-Loaded Microparticles from Polylactide Polymer and 6 g/l Surfactant One gram of poly-L-lactide polymer and nine grams of progesterone were dissolved in ten milliliters of methylene chloride to form an organic phase. In a 4,000 ml beaker, a continuous phase was prepared by dissolving 12 grams of polyvinyl alcohol (PVA) as a surfactant in 2,000 ml of distilled water to yield a concentration of PVA of 0.6% (w/v). The aqueous phase was stirred at 610 rpm at room temperature, i.e., 20° C. The organic phase was then slowly added to the aqueous phase. After one minute of mixing, the stirring speed was reduced to 375 rpm. Ten minutes after the speed of mixing was reduced, 1,000 ml of distilled water at room temperature was added. Sixty minutes after speed reduction, 700 ml of distilled water was added at 80° C. Four and one half hours later, the microparticles were collected on a sieve, washed several times with distilled water, and then air dried. A total of 8.75 grams of progesterone-loaded microparticles was collected. Microparticles having a diameter of 105–150 µm were then obtained by the use of a sieve. This method aimed at loading enough progesterone in the microparticles to constitute theoretically 90% (w/w) of the weight of the microparticles. The recovered progesterone-loaded microparticles were assayed by high pressure liquid chromatography and found to contain 86.5% (w/w) progesterone and 0.18% (w/w) residual polymer solvent.

Preparation of 76% Progesterone-Loaded Microparticles Containing Reduced Residual Polymer Solvent Content, Using 2 g/l Surfactant and Programmed Heating A 65:35 poly-L-lactide:co-glycolide (PLA-PGA) polymer was procured from Birmingham Polymers, Inc. (Lot No. 115–62-1). Five grams of the polymer and 20.0 grams of progesterone were dissolved in 50 ml of methylene chloride to form a discontinuous phase. In a 20 liter glass container an aqueous phase was prepared by dissolving enough polyvinyl alcohol (PVA) in distilled water to prepare 15 liters of solution at 0.2% (w/v) concentration.

The methylene chloride phase was introduced into the continuous phase via a long neck funnel, and the resulting emulsion was stirred at 1,350 rpm. The temperature was increased at a rate of 1.44° C. per hour until the temperature reached 45° C. The system was allowed to remain at this temperature for 60 minutes. At the end of the 60 minute period, 500 ml of room temperature distilled water was added, and the suspension was allowed to cool gradually. When the temperature dropped below 35° C., the microparticles were sieved, washed with distilled water, and then dried. This method aimed at loading enough progesterone in the microparticles to constitute theoretically 80% (w/w). Sieve analysis showed that more than 87% of the progesterone-loaded microparticles were between 25–150 microns in diameter. The progesterone content of the microparticles was found to be 76.2% (w/w). The residual polymer solvent content of the microparticles was 0.08% (w/w).

Preparation of Clonazepam Microparticles Using Programmed Heating

A 65:35 poly-DL-lactide:co-glycolide (PLA-PGA) polymer was procured from Birmingham Polymers, Inc. (Lot No. 107–45-1). A total of 2.95 grams of polymer and 11.8 grams of clonazepam were dissolved in 10 ml of hexafluoroisopropanol and 64 ml of methylene chloride to form an organic phase. In a 4 liter glass beaker, an aqueous phase was prepared by dissolving enough polyvinyl alcohol (PVA) in distilled water to prepare 2,000 ml of 0.8% (w/v) PVA concentration. The aqueous phase was stirred thoroughly at 500 rpm.

The organic phase was added to the continuous phase via a long neck funnel to form an emulsion. After 15 minutes of mixing at 500 rpm, the speed was reduced to 300 rpm. The temperature of the suspension was slowly raised to 45° C. at a rate of 10° C. per hour. The microparticles were collected on sieves after 4 hours. This method aimed at loading enough clonazepam in the microparticles to constitute theoretically 80% (w/w). Sieve analysis showed that 81.6% of the microparticles were in the 25–150 μm size range. The 105–150 μm microparticles were assayed in triplicate, and the clonazepam content found to be 77.2% (w/w).

Preparation of Progesterone Microparticles Using 0.6 g/l PVA Surfactant and Programmed Heating An organic phase was prepared by dissolving 20 grams of progesterone and five grams of 65:35 PLA-PGA (approximately viscosity of 0.99 dl/gram) in 50 ml of methylene chloride in a 250 ml Erlenmeyer flask. In a 17 liter beaker, an aqueous phase was prepared by dissolving enough PVA surfactant in distilled water to prepare 15 liters of a PVA solution at a concentration of 0.6 g/l (w/v).

The organic phase was introduced into the aqueous phase via a long neck funnel to form an emulsion. The emulsion was stirred at 1,350 rpm. This speed was continued for five minutes and then reduced to 950 rpm. After five more minutes at 950 rpm, the speed was reduced to 650 rpm for the duration of the run. The temperature of the suspension was slowly raised at a rate of 1.44 degrees per hour until it reached 45° C. At this time the microparticles were collected and sieved. This method aimed at loading enough progesterone in the microparticles to constitute theoretically 80% (w/w). Nearly 84% of the theoretical amount of microparticles was recovered. Assay of these microparticles showed a drug loading of 71.6% (w/w) and a residual polymer solvent content of 0.097% (w/w).

Preparation of 80% (w/w) Methadone-Loaded Microparticles Using 5 g/l PVA Surfactant and Programmed Heating An organic phase was formed by dissolving 9.36 grams of methadone free base and 1.64 grams poly-L-lactic acid in 16 ml of methylene chloride. A 4,000 ml beaker was filled with an aqueous phase consisting of 2,000 ml of a solution of 0.5% (w/v) polyvinyl alcohol. The organic phase was introduced into the aqueous phase to form an emulsion. An initial stirring speed at the time of addition was 850 rpm. After ten minutes, the stirring speed was lowered to 450 rpm. After 15 minutes at 450 rpm, the temperature of the suspension was slowly raised at a rate of 1.44 degrees per hour until it reached 45° C. When the suspension temperature reached 45° C., the heating was stopped, and the suspension was allowed to cool to room temperature before collecting the microparticles. This method aimed at loading enough methadone in the microparticles to constitute theoretically 80% (w/w). Assay of methadone level showed a loading of 84% (w/w).

Preparation of β-Estradiol-Loaded Microparticles Using 6 g/l PVA Surfactant, Programmed Heating and a Hydrocarbon Solvent Extraction Agent in the Continuous Phase An organic phase was prepared by dissolving a total of 8 grams of 85:15 PLA-PGA polymer in 80 ml methylene chloride, then adding 12 grams of β-estradiol. A 17 liter glass container was filled with 16 liters of an aqueous solution containing 6 g/l polyvinyl alcohol, as a surfactant and 40 ml/l ethanol, as a hydrocarbon extraction agent for the polymer solvent methylene chloride. The organic phase was added to the aqueous phase via a long neck funnel inserted into the aqueous phase to form an emulsion. The emulsion was stirred at 850 rpm. After three minutes, the stirring speed was dropped to 600 rpm, and the heating unit was turned on. The suspension was heated at a rate of 1.46° C. per hour for 18 hours. After 18 hours, the temperature was held constant for one hour at 45° C., and then the emulsion was allowed to cool to room temperature before collection and drying of the microparticles. The microparticles were found to contain a very low amount of residual polymer solvent, i.e. 0.02% (w/w), the β-estradiol content was 57.6% (w/w).

Preparation of Naltrexone Loaded Microspheres

Ten grams of poly-L-(−)-lactide-co-glycolide (65:35) was dissolved in 120 ml of methylene chloride, 30.0 g of naltrexone base were added and dissolved with shaking. Separately, 2,700 ml of a 10% aqueous polyvinyl alcohol solution was added to 30,000 ml of distilled water in a large reaction vessel and brought to 21° C.±2° C. The mixture was stirred at 510 rpm with two 6-blade stainless steel propellers. The naltrexone-polymer solution was poured into the alcohol-water solution, using a long stemmed funnel. The organic solution was dispersed into spherical droplets by agitation. The rate of stirring was maintained for 6 hours, until the droplets hardened through evaporation of the methylene chloride. The microspheres were pumped from the vessel into the 12 inch stainless steel collection sieves. The microspheres were then washed with distilled water. The microspheres with diameters of 105 to 150 μm were filtered onto Whatman Number 4 filter paper and allowed to dry at room temperature. Drying was continued in the clean room for a least 48 hours. The microspheres were then transferred to glass storage containers and weighed. The microspheres were assayed for naltrexone content by HPLC and found to contain 68.2% naltrexone.

Preparation of Nalmefene Loaded Microspheres 1

Ten grams of poly-L-(−)-lactide-co-glycolide (65:35) was dissolved in 120 ml of a mixture of 10% hexafluoroisopropanol in methylene chloride, 30.0 g of nalmefene base was added and dissolved with shaking. Separately, 2,700 ml of a 10% aqueous polyvinyl alcohol solution was added to 30,000 ml of distilled water in a large reaction vessel and brought to 21° C.±2° C. The mixture was stirred at 510 rpm with two 6-blade stainless steel propellers. The nalmefene-polymer solution was poured into the polyvinyl alcohol-water solution, using a long stemmed funnel. The organic solution was dispersed into spherical droplets by agitation. The rate of stirring was maintained for 6 hours, until the droplets hardened through evaporation of the organic solvents. The microspheres were pumped from the vessel into the 12 inch stainless steel collection sieves. The microspheres were then washed with distilled water. The microspheres with diameters of 105 to 150 µm were filtered onto Whatman Number 4 filter paper and allowed to dry at room temperature. Drying was continued in the clean room for a least 48 hours. The microspheres were then transferred to glass storage containers and weighed. The microspheres were assayed for nalmefene content by HPLC and found to contain 76.1% nalmefene.

Preparation of Nalmefene Loaded Microspheres 2

Ten grams of poly-L-(−)-lactide-co-glycolide (65/35) was dissolved in 120 ml of a mixture of 10% dimethylsulfoxide in methylene chloride, 30.0 g of nalmefene base was added and dissolved with shaking. Separately, 2,700 ml of a 10% aqueous polyvinyl alcohol solution was added to 30,000 ml of distilled water in a large reaction vessel and brought to 21° C.±2° C. The mixture was stirred at 510 rpm with two 6-blade stainless steel propellers. The nalmefene-polymer solution was poured into the polyvinyl alcohol-water solution, using a long stemmed funnel. The organic solution was dispersed into spherical droplets by agitation. The rate of stirring was maintained for 6 hours, until the droplets hardened through evaporation of the organic solvents. The microspheres were pumped from the vessel into the 12 inch stainless steel collection sieves. The microspheres were then washed with distilled water. The microspheres with diameters of 105 to 150 µm were filtered onto Whatman Number 4 filter paper and allowed to dry at room temperature. Drying was continued in the clean room for a least 48 hours. The microspheres were then transferred to glass storage containers and weighed. The microspheres were assayed for nalmefene content by HPLC and found to contain 74.9% nalmefene.

Preparation of Buprenorphine Loaded Microparticles

A core microparticle was prepared by mixing together, as a slurry, buprenorphine base with 65/35 poly-L(−)lactide-co-glycolide in a ratio of 80% drug and 20% polymer using methylene chloride as the solvent. This material was then cast onto a glass plate for drying. While drying, the material was turned over repeatedly to prevent domains from forming. After the core dried, it was ground with dry ice until the microparticles were between 50–150 µm in size. The microparticles were collected and sieved using the wet sieving method. The microparticles that were greater than 150 µm were reground and those that were less than 50 µm were recast and reground. The Buprenorphine content of the microparticles was 80%.

Preparation of Testosterone Loaded Microspheres

Five grams of poly-D,L-lactide-co-glycolide (85:15) were dissolved in 50.0 ml of methylene chloride. After dissolution of the polymer 20.0 g of testosterone USP was added and dissolved with shaking. Separately, 900 ml of a 10% aqueous polyvinyl alcohol was added to 14,100 ml of distilled water in a large cylinder jar, and brought to 23° C.±2° C. The mixture was stirred at 1,350 rpm with a 6-blade stainless steel propeller, then the testosterone-polymer solution was poured in. The organic solution was dispersed into spherical droplets by the agitation. After about 5 minutes the rate of stirring was reduced to 950 rpm for 5 minutes and then reduced to 650 rpm and maintained there for two or more hours, until the droplets harden through evaporation of the methylene chloride. The microspheres were allowed to settle and the supernatant was decanted. The microspheres were washed with distilled water and decanted. Next, the microspheres were wet-sieved with distilled water and separated into various size fractions. The appropriate fraction (105–150 mm) was filtered onto a Whatman No. 4 filter paper and allowed to dry at room temperature. Microspheres were transferred to glass containers and weighed. The above procedure was repeated several times until a sufficient quantity of microspheres (about 10 g) of the specified size had been accumulated for coating in the pilot coating equipment. Testosterone microspheres were characterized by size distribution, and assayed for testosterone content which was found to be above 75%.

EXAMPLE III

Preparation of a Microparticle Having a Polymer-Drug Layer

One or more coating layers, i.e. 2, 3, 4, 5, 6, 7, 8, 9, 10 or more, applied on the microparticle core of Example I or II may contain a biodegradable, pharmaceutically acceptable polymer, an active ingredient or a mixture of a polymer and active ingredient. The mixture may vary in the concentration of the polymer and active ingredient, for example from 1 to 99% or 5 to 95%, or more typically, the active ingredient content of the coating layer generally would be greater than 50%, 60%, 70%, 75%, 80%, 85% or greater by weight of the microcapsule. The amount of the polymer and the active ingredient may vary as desired, and may be the same or different in each coating layer. Additionally, the microcapsule may contain coating layers with increasing or decreasing concentrations of an active ingredient, and the coating layer may contain the same or different polymer or active ingredient. Coating layers including outer wall layers may also include lipids, waxes, gels and other materials known in the art to serve as coating layers. Methods of applying such coating layers to microparticles are known to those skilled in the art.

The microcapsule may contain a high drug concentration layer contiguous to a low drug concentration layer, however it is recognized that the polymer layers may contain different drugs at the same concentration, or a plurality of different layers of varying drug concentrations and types, to obtain a desired release profile. A high drug concentration layer may contain 70% to 95% or even 100% of a drug by weight and a low drug concentration layer uniformly coated on a preceding layer may contain, 30–70% by weight. Preferably, the layer coating the microparticle core will contain the same or substantially the same polymer as the microparticle core to provide for suitable adhesion between the layer and the polymer core. Likewise, contiguous layers will also preferably contain the same or substantially the same polymers to provide for suitable adhesion.

The polymer-drug layer is typically applied to the microparticle core by a spray coating technique in a custom fluidized bed coating apparatus described as follows with reference to FIG. 1. A starting microparticle core 12 of Example I is directed into apparatus 22 which is referred to herein as a fluidized bed air suspension apparatus having a funnel-shape with a wider upper member 24 and a narrower tube-like lower member 26. The microparticle core 12 is directed into the lower member 26 from an outside source 28 and is carried upward by air directed through an air distribution plate 30 into a central cylindrical coating area 32 of the lower member 26. In the coating area 32 a solution of about 80% active ingredient, such as estradiol, and 20% polymer, such as a PLA-PLG copolymer in acetone, methylene chloride solvent is sprayed from a hydraulic or pneumatic nozzle 34 within the air distribution plate 30 and collides with the microparticle core. An air stream 36 from the air distribution plate 30 carries the coated-core particle 38 into the upper member 24 drying area 42 of the apparatus 22 and back downward into an annular ring 40 surrounding the central cylindrical coating area 32 of the lower member 26.

Core microparticles 12 are recycled through the apparatus 22 to receive a coating increment with each complete cycle until the concentration of drug reaches the preferred loading typically 5% to 85% of the microparticle weight. In one example, the polymer-drug coating is composed of an admixture, for example, of 70–95% by weight of a drug such as estradiol and the remaining of a poly-l-lactide or co-glycolide polymer which is spray coated onto the polymer core.

A microcapsule according to the teachings of the present invention is prepared according to the following method. Estradiol microcapsules comprise a polymer core and a coating of drug and polymer. In the first step, polymer microsphere core is prepared according to the procedure described in Example I. The core microspheres are prepared by solvent evaporation. Since no drug is present in the microspheres, excess solvent, such as methylene chloride, can be removed in the second step by heating the core microspheres to 80° C. for several hours. Methylene chloride is used in the core production process because it is immiscible with water and a good solvent for PLG polymers.

In the third step, microsphere cores in a selected size range (50–75 μm for example) are placed in the microfluidized bed unit and an acetone solution containing estradiol and PLG in the ratio 4:1 is sprayed onto the microparticles until the concentration of estradiol in the microparticles approaches 60%.

A typical run would be as follows. Five grams of polymer core microspheres are charged into the coating chamber. Two hundred fifty milliliters of a 4% estradiol/1% poly-DL-lactide-co-glycolide in acetone solution is sprayed onto the polymer core. When all the solution is sprayed, the microspheres are collected and wet sieved onto 8" stainless steel sieves for size classification. The material is assayed for estradiol drug loading and blended together for overcoating with polymer.

EXAMPLE IV

Preparation of a Microcapsule Having a Polymer-Drug Core and Polymer Wall

The microcapsules of the preceding Examples may be provided with one or more polymer wall layers according to the spray-coating procedure set forth in Example III. Where an outer polymer wall layer is employed, the thickness of the wall coating is usually selected to provide for the sustained or controlled release of active ingredient in the microcapsule; and may, for example, vary from 0.1–85% by total weight of the microcapsule, and typically depends on the size of the microcapsule being employed. Polymer wall layers are typically in the range of thickness of from 1 to 10 microns and preferably are composed of the same or substantially the same polymer as used in the preceding layer to insure adhesion to the preceding layer. Polymer wall layers within the scope of the present invention include porous-type polymer wall layers that permit the increased rate of release of active ingredient from polymer-drug layers. Outer polymer wall layers are comprised of a same or similar polymer as an underlying layer and may include a plasticizer or a drug or other water-leachable material or water-soluble plasticizers, such as polyethylene glycols, or other pharmaceutically acceptable products to include salts, so that when the microcapsule is in use, the leachable material will be leached out of the polymer wall to increase the rate of release of the drug in the microcapsule.

According to one embodiment of the present invention, a microcapsule contains an inner polymer microparticle core covered by a first polymer drug layer followed by a polymer wall layer over the first polymer-drug layer further followed by a second polymer-drug layer covered by an outer polymer wall layer to form an onion-skin type composite microcapsule. The drugs in the polymer-drug layers may be the same or different, and may be in the same or different concentrations. Alternatively, the drug containing layers may be absent of polymer or may contain other pharmaceutically-acceptable material.

Polymer coating layers, including outer polymer wall layers are applied to the microcapsule of Example I or II using the same fluidized bed air suspension apparatus 22 that is used to apply the polymer-drug coating layer. However, the outside source 28 is now filled with microcapsules having a microparticle core alone or in combination with a polymer-drug coating as prepared according to Example III. The microcapsules 38 are released into the central cylindrical spray-coating area 32 and are carried by the airstream 36. PLA-PGA polymer in acetone solvent is sprayed through the hydraulic air pneumatic nozzle 34 and collides with the microcapsules 38. Successive layers of PLA-PGA polymer covering the microcapsules 38 form a rate-controlling membrane wall that determines the rate of drug release from the microcapsules. The final sustained-release microcapsule size is within a range of 25 to 200 microns in diameter and well suited to delivery of a plurality of such microcapsules within a liquid suspension carrying medium by a standard hypodermic needle. Residual acetone solvent within the microcapsules was found to be released during use within a mammal at a rate of approximately 3 milligrams per 100 milligrams of user body weight.

Preparation of Testosterone Microcapsules by Coating Testosterone Microspheres with Polymer Coating of testosterone microspheres by air suspension coating is as follows.

The solution used for coating is a 1% solution of poly-D,L-lactide-co-glycolide (85:15) in acetone. Ten grams of testosterone microspheres prepared according to the procedure in Example II are loaded into the microfluidized bed equipment. The microspheres are fluidized by air at ambient temperature (65–75° F.). The amount of coating solution applied is calculated from the microsphere input and the target coating level. For example, if 10 g of microspheres are coated to a target level of 10%, about 100 ml of a 1% coating solution are sprayed. After the coating is completed the microcapsules are hardened by evaporation the residual acetone. After removal from the coating equipment, they are characterized by to size, testosterone content, residual solvent content, and rate of drug release in vitro after irradiation. The effect of coating on the rate of release and duration of delivery of the drug from the microspheres and microcapsules is shown in FIG. 3. The final testosterone content of the microcapsules was 74.4%. This formulation delivered a therapeutic level of testosterone in seven men with hypogonadism for a period of 70 days (see FIG. 4).

Preparation of Naltrexone Microcapsules by Coating Naltrexone Microspheres with Polymer The coating solution for the naltrexone microspheres prepared in Example II is a 1% solution of poly-L-(−)-lactide-co-glycolide (65:35) in acetone. After loading about 8 g of naltrexone microspheres into the microfluidized bed equipment, the bed is fluidized by air at ambient temperature (65 to 75° C.). The amount of coating applied is calculated from the microsphere input and the target coating level (14%). If 8 g of microspheres are coated to a theoretical coating level of 14%, approximately 112 ml of a 1% coating solution will be sprayed. After the coating is completed the microcapsules are hardened by evaporation of the residual acetone. After removal from the coating equipment, the microcapsules are characterized by to size, naltrexone content, residual solvent content, and rate of drug release in vitro after irradiation. The final naltrexone content of the microcapsules was 54.4%. This formulation delivered a therapeutic level of naltrexone in six heroin addicts for a period of 30 days (see FIG. 7).

Preparation of Buprenorphine Microcapsules by Coating Buprenorphine Microspheres with Polymer The buprenorphine 50–150 μm microparticle core prepared in Example II was overcoated to a theoretical 3% level using a fluidized bed coating chamber. A total of six coating runs were made. The overall yield of microcapsules in the six runs was 87.7%, with an average of 60.6% in the desired 50–150 μm size range. The buprenorphine content of the six runs averaged 74.2±3.6%. FIG. 8 is a graphic representation of the blood level of buprenorphine in five heroin addicts given a single depot dose of buprenorphine microcapsules. FIG. 9 is a graphic representation of the effect of a single injection of microcapsules containing 58 mg of buprenorphine on visual analog scaling (VAS) drug effect in response to opioid challenge in five heroin addicts.

EXAMPLE V

Preparation of a Microcapsule Having a Polymer Drug Core and Polymer-Drug Layer

The coating solution for the nalmefene microspheres prepared in Example II is an acetone solution composed of 2% nalmefene and 1% of poly-L-(−)-lactide-co-glycolide (65:35). After loading about 8 g of nalmefene microspheres into the microfluidized bed equipment, the bed is fluidized by air at ambient temperature (65 to 75° C.). The amount of coating applied is calculated from the microsphere input and the target coating level. After the coating is completed the microcapsules are hardened by evaporation the residual acetone. After removal from the coating equipment, they are characterized by size, nalmefene content, residual solvent content, and rate of drug release in vitro after irradiation. The final nalmefene content of the microcapsules was 77%. The in vitro release of nalmefene from this formulation and from another formulation containing 5% nalmefene in the polymer wall is shown in FIG. 5. Following injection of the microcapsules the response of rhesus monkeys to morphine challenge was reduced for a period of 40 days (see FIG. 6).

EXAMPLE VI

Preparation of a Microcapsule Having a Polymer-Drug Layer and Polymer Wall

Estradiol microparticles which have been prepared by coating polymer microspheres with a mixture of estradiol and polymer are prepared as described in Example III. The solution used for coating is a 1% solution of poly-DL-lactide-co-glycolide (85:15) in acetone. After loading about 8.0 g of estradiol microspheres (75–150 μm) into the coating equipment, the bed is fluidized by air at ambient temperature (65–75° F.). The volume of the coating solution applied is calculated from the microsphere input and the target coating level (10%). After coating, the microcapsules are dried in the fluidized bed equipment. They are then collected and wet sieved onto stainless steel sieves for size classification. The estradiol microcapsules are then characterized by size, estradiol content, and rate of drug release in vitro after irradiation. Estradiol microcapsules prepared by this method contained 53.4% estradiol drug. The residual methylene level was 0.74%. FIG. 2 shows the blood level of estradiol in five postmenopausal women. The level remained above the therapeutic level for a period of 20 weeks.

It is to be understood that embodiments of the present invention that have been described are merely illustrative of some applications of the principles of the present invention. Numerous modifications may be made by those skilled in the art without departing from the true spirit and scope of the invention.

What is claimed is:

1. A method of making coated microparticles comprising mixing a biodegradable polymer, naltrexone, and methylene chloride to form an organic phase,
mixing the organic phase with an aqueous phase to form an emulsion,
maintaining the emulsion for a period of time sufficient to form hardened microparticles,
recovering the microparticles, and
coating the microparticles with a coating polymer to form a polymer coating in an amount between 0.1 to 85 percent by weight of the microparticles wherein the biodegradable polymer is a member selected from the group consisting of D or L optically active forms or DL optically inactive forms of poly-lactide (PLA), poly-lactide-co-glycolide (PLA-PGA) polymers, or poly-L-lactide-co-caprolactone (PLA-PCL) polymers and wherein the naltrexone is present in an amount of between greater than 50 and 85 weight of the microparticles.

2. The method of claim 1 wherein the polymer coating is in an amount of 14% by weight of the microparticles.

3. The method of claim 1 wherein the polymer coating is in an amount of 10% by weight of the microparticles.

4. The method of claim 1 wherein the polymer coating is in an amount of 3% by weight of the microparticles.

5. The method of claim 1 wherein the naltrexone is in an amount of 70% by weight of the microparticles.

6. The method of claim 1 wherein the naltrexone is in an amount of 75% by weight of the microparticles.

7. The method of claim 1 wherein the naltrexone is in an amount of 80% by weight of the microparticles.

8. The method of claim 1 wherein the naltrexone is in an amount of 85% by weight of the microparticles.

9. Coated microparticles made according to a process comprising mixing a biodegradable polymer, naltrexone and methylene chloride to form an organic phase,
mixing the organic phase with an aqueous phase to form an emulsion,
maintaining the emulsion for a period of time sufficient to form hardened microparticles,
recovering the microparticles, and
coating the microparticles with a coating polymer to form a polymer coating in an amount between 0.1 to 85 percent by weight of the microparticles wherein the biodegradable polymer is a member selected from the group consisting of D or L optically active forms or DL optically inactive forms of poly-lactide (PLA), poly-lactide-co-glycolide (PLA-PGA) polymers, or poly-L-lactide-co-caprolactone (PLA-PCL) polymers and wherein the naltrexone is present in an amount of between greater than 50 and 85 weight of the microparticles.

10. The coated microparticles of claim 9 wherein the polymer coating is in an amount of 14% by weight of the microparticles.

11. The coated microparticles of claim 9 wherein the polymer coating is in an amount of 10% by weight of the microparticles.

12. The coated microparticles of claim 9 wherein the coating polymer is in an amount of 3% by weight of the microparticles.

13. The coated microparticles of claim 9 wherein the naltrexone is in an amount of 70% by weight of the microparticles.

14. The coated microparticles of claim 9 wherein the naltrexone is in an amount of 75% by weight of the microparticles.

15. The coated microparticles of claim 9 wherein the naltrexone is in an amount of 80% by weight of the microparticles.

16. The coated microparticles of claim 9 wherein the naltrexone is in an amount of 85% by weight of the microparticles.

17. A method of making coated microparticles comprising
mixing a biodegradable polymer, nalmefene, methylene chloride and dimethyl sulfoxide to form an organic phase,
mixing the organic phase with an aqueous phase to form an emulsion,
maintaining the emulsion for a period of time sufficient to form hardened microparticles,
recovering the microparticles, and
coating the microparticles with a coating polymer to form a polymer coating in an amount between 0.1 to 85 percent by weight of the microparticles wherein the biodegradable polymer is a member selected from the group consisting of D or L optically active forms or DL optically inactive forms of poly-lactide (PLA), poly-lactide-co-glycolide (PLA-PGA) polymers, or poly-L-lactide-co-caprolactone (PLA-PCL) polymers and wherein the nalmefene is present in an amount of between greater than 50 and 85 by weight of the microparticles.

18. The method of claim 17 wherein the polymer coating is in an amount of 14% by weight of the microparticles.

19. The method of claim 17 wherein the polymer coating is in an amount of 10% by weight of the microparticles.

20. The method of claim 17 wherein the coating polymer is in an amount of 3% by weight of the microparticles.

21. The method of claim 17 wherein the nalmefene is in an amount of greater than 70% by weight of the microparticles.

22. The method of claim 17 wherein the nalmefene is in an amount of greater than 75% by weight of the microparticles.

23. The method of claim 17 wherein the nalmefene is in an amount of greater than 80% by weight of the microparticles.

24. The method of claim 17 wherein the nalmefene is in an amount of 85% by weight of the microparticles.

25. Coated microparticles made according to a process comprising
mixing a biodegradable polymer, nalmefene, methylene chloride and dimethyl sulfoxide to form an organic phase,
mixing the organic phase with an aqueous phase to form an emulsion,
maintaining the emulsion for a period of time sufficient to form hardened microparticles,
recovering the microparticles, and
coating the microparticles with a coating polymer to form a polymer coating in an amount between 0.1 to 85 percent by weight of the microparticles wherein the biodegradable polymer is a member selected from the group consisting of D or L optically active forms or DL optically inactive forms of poly-lactide (PLA), poly-lactide-co-glycolide (PLA-PGA) polymers, or poly-L-lactide-co-caprolactone (PLA-PCL) polymers and wherein the nalmefene is present in an amount of between greater than 50 and 85 by weight of the microparticles.

26. The coated microparticles of claim 25 wherein the polymer coating is in an amount of 14% by weight of the microparticles.

27. The coated microparticles of claim 25 wherein the polymer coating is in an amount of 10% by weight of the microparticles.

28. The coated microparticles of claim 25 wherein the coating polymer is in an amount of 3% by weight of the microparticles.

29. The coated microparticles of claim 25 wherein the nalmefene is in an amount of greater than 70% by weight of the microparticles.

30. The coated microparticles of claim 25 wherein the nalmefene is in an amount of 75% by weight of the microparticles.

31. The coated microparticles of claim 25 wherein the nalmefene is in an amount of 80% by weight of the microparticles.

32. The coated microparticles of claim 25 wherein the nalmefene is in an amount of 85% by weight of the microparticles.

* * * * *